US00PP10655P

United States Patent [19]

Egger

[11] Patent Number: Plant 10,655

[45] Date of Patent: Oct. 20, 1998

[54] ASIATIC HYBRID LILY PLANT NAMED 'RED SPIDER'

[75] Inventor: Donald L. Egger, Wilsonville, Oreg.

[73] Assignee: Cebeco Lilies, Inc., Aurora, Oreg.

[21] Appl. No.: 788,951

[22] Filed: Jan. 23, 1997

[51] Int. Cl.[6] ..... A01H 5/00

[52] U.S. Cl. ..... Plt./87.4

[58] Field of Search ..... Plt./87.4

*Primary Examiner*—James R. Feyrer

*Assistant Examiner*—Kent L. Bell

*Attorney, Agent, or Firm*—Klarquist Sparkman Campbell Leigh & Whinston, LLP

[57] ABSTRACT

A new and distinct bicolor tetraploid Asiatic lily hybrid for cut flower production having numerous, upright, red flowers with a red orange blush on tall strong stems.

2 Drawing Sheets

BACKGROUND OF THE INVENTION

The present invention relates to a new and distinct cultivar of lily hybrid referred to commercially as an upright flowering tetraploid Asiatic hybrid lily and given the cultivar name 'Red Spider.'

This invention was developed by controlled breeding in Aurora, Oreg. using 'Gran Paradiso' as the seed parent and 'Tetra Connecticut King' as the pollen parent.

This invention has not been observed under all possible environmental conditions. The phenotype may vary significantly with variations in environment such as temperature, light intensity and day length, without, however, any variation in genotype.

The following traits have been repeatedly observed and are determined to be the basic characteristics of this invention which in combination distinguish this lily as a new and distinct cultivar: (1) large, tetraploid, red flowers with an orange blush; (2) large red buds; (3) high bud count; (4) early bloom time; (5) short leaves, better for low light forcing; (6) very strong stems; (7) shows excellent bulb cold storage. In addition, this invention shows good disease resistance. Bulbs of this plant may be precooled and forced out of season for very uniform cut flower production.

Compared to 'Gran Paradiso,' this invention has bigger flowers, better color, earlier bloom time and better bud color. Unlike 'Gran Paradiso', this invention does not produce multiple aborted sepals. Also, to the inventor's knowledge, there are no other tetraploid Asiatic lilies with bicolor flowers on the market commercially.

Asexual reproduction of this new variety has been accomplished at Cebeco Lilies, Inc., Aurora, Oreg. by scaling and tissue culture. The resulting plants have shown that the abovementioned unique features are stable and reproduce true to type in each successive propagation.

BRIEF DESCRIPTION OF THE DRAWING

FIG. 1 is a photograph showing the 'Red Spider' lily.

FIG. 2 is a close-up photograph which illustrates in greater detail a single flower of the new plant.

The photographs of the drawing were taken in June 1995 in a studio and illustrate the typical flower and foliage form, with color as true as reasonably possible in this type of color photograph.

DETAILED DESCRIPTION

The following is a detailed description of the invention based on plants produced in accordance with generally accepted commercial practices at the Cebeco Lilies, Inc. research station in Aurora, Oreg. in June 1995. Color references are made to The Royal Horticultural Society Colour Chart, except where the context indicates a term having its ordinary dictionary meaning.

The Plant

Origin: Seedling.

Parentage:

*Seed parent.*—'Gran Paradiso'.

*Pollen parent.*—'Tetra Connecticut King'.

Commercial classification: Hybrid Asiatic Lily, Tetraploid cut flower type.

Classification: Division I-A, Upright facing Asiatic hybrid lily, according to The Horticultural Classification of Lilies by The Royal Horticultural Society of London.

Form: Single erect stem bearing terminal cluster of flowers.

Height: About 95–115 cm. from the top of the soil to the top of the flowers from bulbs of 12 cm. in circumference.

Stem color: Yellow green mottled with maroon. Yellow-Green Group 144A.

Growth habit: Vigorous, upright and rigid.

Foliage:

*Arrangement.*—Spiral.

*Leaf size.*—To about 82 mm. long and 16 mm. wide.

*Leaf shape.*—Lanceolate.

*Texture.*—Leathery.

*Aspect.*—Glossy.

*Color.*—Medium green on both sides, lighter on the back. Closest to Yellow Green Group 147A.

Bulbs:

*Size.*—Variable, ranging to about 12–14 cm. in circumference as used commercially.

*Color.*—White.

The Bud

Size: Large. To about 85 mm. long and 27 mm. wide just prior to opening.

Shape: Ovoid with an obtuse tip.

Rate of opening: The mature bud opens slowly in response to light.

Color: Red. Overall color is closest to Grayed-Red Group 179A with top half darker, Red Group 46A and base and margins lighter, Red Group 34B.

The Flower

Blooming habit: Annually, once and early season.

Days to bloom : Flowers approximately 80 days after spring greenhouse planting under typical commercial flower forcing conditions of 15 degrees Celsius night time temperatures.

Inflorescence size: About 27 cm. high and 23 cm. wide when there are nine flowers present.

*Flower size: Large.*

*Diameter.*—About 16 cm.

*Depth.*—About 2.5 cm.

Borne: In a modified raceme of 9 flowers from bulbs 12–14 cm. in circumference.

Shape: When the flower first opens it is bowl shaped. Later the bowl flattens out and the tepals reflex at the tips.

Tepalage:

*Number.*—Six.

*Arrangement.*—Imbricated.

*Shape.*—Ovate.

*Texture.*—Spongy, waxy, thick.

*Aspect.*—Satiny. glossy.

*Size.*—Length: About 90 mm. Width: Inner tepals — about 52 mm. Depth of imbrication: About 20 mm.

*Nectary.*—About 22 mm. long; dark red, Red Group 47A; glandular pubescent; channels together.

*Projections.*—Some present on either side of the nectary as raised lines.

*Spots.*—None to one on some inner tepals.

*Blush.*—Above the nectary, orange, Orange-Red Group 30B.

*Color.*—Topside: Red with and orange blush. Red Group 42A with blush as described above. Bottomside: Red with orange red near midrib. Orange — Red Group 34A with Orange-Red Group 33B around midrib.

*Discoloration.*—Darkens with age.

*Fragrance.*—None.

Pedicle:

*Length.*—About 7–9 cm.

*Color.*—Yellow green the same as the stem, heavily covered with hairs.

*Orientation.*—Ascending upwardly to about 45° from the horizontal.

The Reproductive Organs

Stamens:

*Number.*—Six, typical of the genus Lilium.

*Anthers before dehiscence.*—Size: About 21 mm. Color: Greyed-Red 181C.

*Filaments.*—Length: About 62 mm. Color: Dark red at top (46A) to red (42C) to orange (24C) at base.

*Pollen.*—Color: Bright red orange. Orange-Red Group 34A.

Pistil:

*Number.*—One.

*Style.*—Length: About 47 mm. Color: Red-Purple Group 64A.

*Stigma.*—Color: Red purple. Grayed-Purple Group 183B.

The Fruit

Fertility: Fertile.

Shape: Ovoid.

Color at maturity: Soft Brown.

I claim:

1. A new and distinct cultivar of Asiatic hybrid lily plant substantially as herein shown and described.

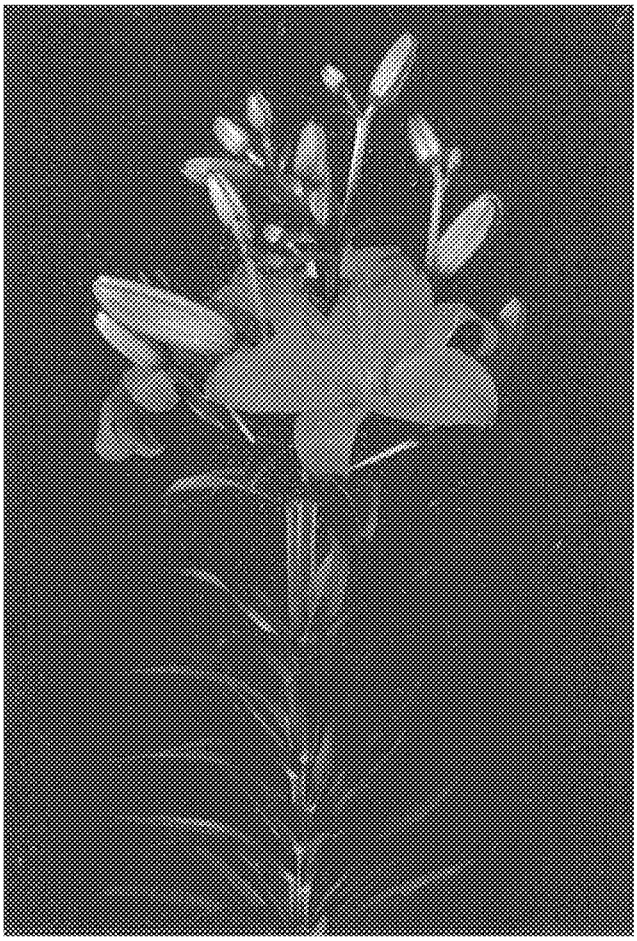

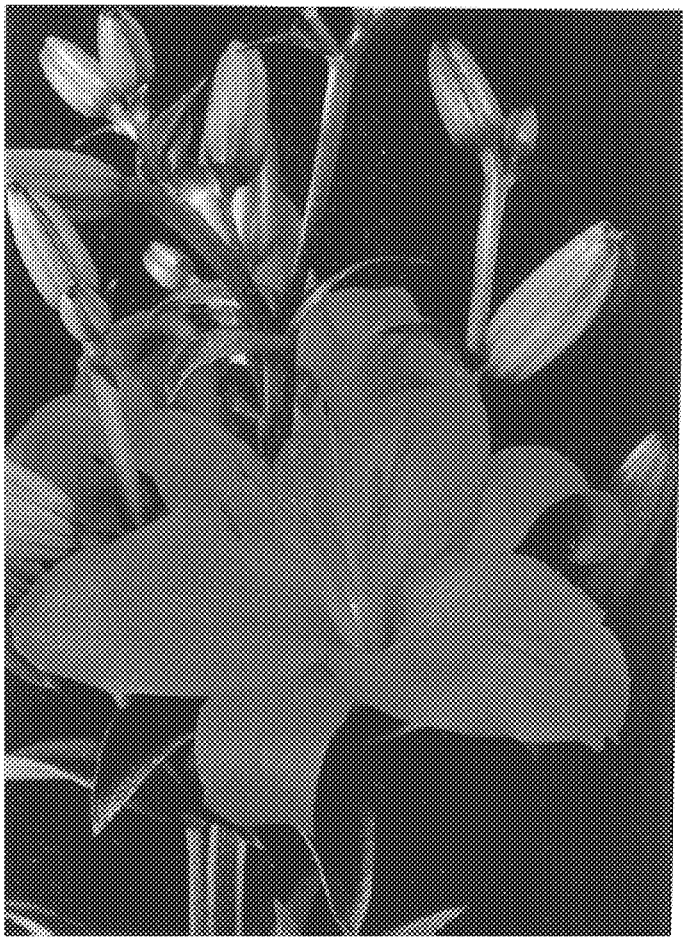

* * * * *